(12) United States Patent
Kita et al.

(10) Patent No.: US 6,334,356 B1
(45) Date of Patent: Jan. 1, 2002

(54) METHOD FOR DECIDING THE VISCOSITY IN THE DENSITY MEASUREMENT

(75) Inventors: Toshiro Kita; Kenji Kawaguchi; Toshiyuki Shimizu, all of Kyoto (JP)

(73) Assignee: Kyoto Electronics Manufacturing Company, Limited, Kyoto (JP)

( * ) Notice: Subject to any disclaimer, the term of this patent is extended or adjusted under 35 U.S.C. 154(b) by 0 days.

(21) Appl. No.: 09/419,101

(22) Filed: Oct. 15, 1999

(30) Foreign Application Priority Data

Oct. 15, 1998 (JP) ............................................. 10-294026

(51) Int. Cl.$^7$ ........................... G01N 9/00; G01N 11/16; G01N 29/02
(52) U.S. Cl. ..................... 73/54.01; 73/54.25; 73/54.41; 73/25.5
(58) Field of Search .............................. 73/54.01, 54.02, 73/54.25, 54.24, 54.41, 61.45, 24.05, 861.355, 861.356

(56) References Cited

U.S. PATENT DOCUMENTS

| | | | | |
|---|---|---|---|---|
| 4,177,669 A | * | 12/1979 | Wenger | 73/32 A |
| 4,331,025 A | * | 5/1982 | Ord, Jr. | 73/54 |
| 4,429,564 A | * | 2/1984 | Ikeda et al. | 73/32 A |
| 4,524,610 A | * | 6/1985 | Fitzgerald et al. | 73/54 |
| 4,566,181 A | * | 1/1986 | Matusik et al. | 29/602 R |
| 4,754,640 A | * | 7/1988 | Fitzgerald et al. | 73/54 |
| 5,317,908 A | * | 6/1994 | Fitzgerald et al. | 73/54.26 |
| 5,533,381 A | * | 7/1996 | Seale | 73/19.03 |
| 5,741,961 A | * | 4/1998 | Martin et al. | 73/32 R |
| 5,827,979 A | * | 10/1998 | Schott et al. | 73/861.357 |
| 6,076,392 A | * | 6/2000 | Drzewiecki | 73/23.2 |

\* cited by examiner

*Primary Examiner*—Hezron Williams
*Assistant Examiner*—David J. Wiggins
(74) *Attorney, Agent, or Firm*—Ronald E. Greigg

(57) ABSTRACT

This invention relates to a method for deciding an amount of correction factor for the viscosity of a fluid test sample needed for correcting a calculation or measurement of the density based on the viscosity.

The method for deciding the viscosity of the fluid test sample, during a density measurement performed by an oscillating densitometer where there is a peak point on the viscosity-attenuation constant characteristic of the test sample at the specific order oscillation, is to decide whether the attenuation constant of the viscosity-attenuation constant characteristic of the test sample at the other specific order oscillation is larger or smaller than that corresponding to the peak point, to decide according to said decision whether the viscosity detected by the attenuation constant obtained at the specific order oscillation belongs to either side larger or smaller than the peak point, and then to decide upon and determine the viscosity of the test sample according to the above two decisions.

2 Claims, 8 Drawing Sheets

($\varepsilon_1 > \varepsilon_2$ when $\theta_1 > \theta_2$)

METHOD FOR DECIDING THE VISCOSITY IN THE DENSITY MEASUREMENT

BACKGROUND OF THE INVENTION

1. Technical Field

This invention relates to a method for deciding a viscosity in case of correcting a density of a fluid test sample in accordance with the viscosity in the density measurement by means of an oscillating densimeter.

2. Description of the Prior Art

An U-shaped tube which is filled at the base ends (the both ends of the upper portion of U) is filled with a test sample (liquid or gas). When the mechanical vibration is given to the U-shaped tube, the tube vibrates in response thereto at the frequency based on the density of the test sample filled inside of the U-shaped tube. Therefore, the viscosity of the test sample can be obtained by measuring the frequency (or the oscillation period). It is the oscillating densimeter that the method of this instant application is applied to.

FIG. 2 shows a basic constitution of a conventional oscillating densimeter. A permanent magnet 11 is fixed on the pointed end (the base portion) of the U-shaped tube 10. Then the electric current with a specific frequency flows into a driving coil 14 provided nearby the permanent magnet the U-shaped tube 10 vibrates.

The vibration of the U-shaped tube 10 is detected by a sensor 13. The detected signals from the sensor 13 is amplified by an amplifier 12 and sent back to the driving coil 14. According to the above constitution, the U-shaped tube is to resonate with the frequency of the electric current in the driving coil. And the oscillating period of the U-shaped tube is measured in accordance with the output signals from the sensor 13, the results of which is offered to the density operation by the calculation means 15.

The density which is obtained easily from the oscillating frequency as described above has the difference based on the viscosity of the test sample as shown in FIG. 4. Namely, the larger the viscosity $\eta$ is, the larger the difference rate represented by $\Delta\rho/\rho_1$ becomes ($\Delta\rho=\rho_1-\rho_0$, where the true value of the density is represented by $\rho_0$ while the measured value is represented by $\rho_1$).

In order to correct the density difference based on the viscosity $\eta$, it is necessary to detect the viscosity of the test sample. The viscosity $\eta$ can be detected in accordance with the relation between the viscosity and the attenuation constant, which is disclosed in IEE TRANSACTIONAL ON INDUSTRIAL ELECTRONICS AND CONTROL INSTRUMENTATION, VOL. IEC1-27, NO. 3, AUGUST 1980, 247–253 (the literature 1). Therefore, the density-attenuation constant characteristic at the 0 order oscillation can be represented by the function $b0=f(\eta)$ or that at the first order oscillation by the function $b1=g(\eta)$ respectively (the "order" will be explained later) as shown in FIG. 5. The 0 order oscillation is a mode that one node of the oscillation is positioned at the base ends of the U-shaped tube, which is shown as i=1 in FIG. 6. In general the density can be obtained in accordance with the frequency of this mode. And the first order oscillation is a mode that there are two nodes which are positioned at the base ends and the position at one quarter to the base ends, and is shovel as i=2 in FIG. 6. And there are also modes at higher order oscillation (i=3 and i=4, for example).

The conventional constitution is arranged in the literature 1 that the circuit as shown in FIG. 7 works in order to generate the oscillation at each mode.

Accordingly, the output from a piezoelectric element 21 as a sensor, that is to say a detected voltage Ud is inputted as signals U into a modulator 24 and a phase shift unit 25 via a variable gain amplifier 22 and a voltage-controlled phase adjuster 23.

And the signals U compose control signals Uc of the variable gain amplifier 22 via a rectifier 22 and an integrator 27. This loop, that is the variable gain amplifier 22→the voltage-controlled phase adjuster 23→the rectifier 26→the integrator 27→the variable gain amplifier 22, is provided with a function for fixing the height of the output U without regard to the height of the detected voltage.

The modulator 24 outputs a value which is an amplitude of the basic signals U multiplied by modulation coefficient $\epsilon$, while the phase shift unit 25 outputs signals that has a phase of the basic signals U shifted to $-\theta$ (45°, for example). Those two signals are added each other at a mixer 28, and then signals Uc can be obtained the phase of which is shifted for the angle corresponding to one of the modulation coefficient $\epsilon_{10}$, $\epsilon_2$ as shown in FIGS. 8a and 8b. By using the signals, the excited current Iexc is to be detected. Namely the signals U is made to delay by 45° via the phase shift unit 25. On the other hands, the signals $\epsilon_1 U$ or $\epsilon_2 U$ (shown as $\epsilon_1 > \epsilon_2$, in FIG. 8a and 8b is multiplied by the modulation coefficient $\epsilon_1$ or $\epsilon_2$ respectively, and the product is added to the basic signals, in a result the signals $Ue_1$ or $Ue_2$ generates. In the signals $Ue_1$ or $Ue_2$, in case of $\epsilon_1 > \epsilon_2$, the delay angle is represented by $\theta_1 > \theta_2$.

And the modulation coefficient $\epsilon$ can be changed by adjusting the value of N of the control signal $\omega/N$ that is inputted into the modulator 24.

If the signals with sifted phases as above are obtained, a resonating frequency with new, phase can be obtained, too. And it is also possible to obtain the higher harmonics of the first order, that is the oscillation of i=2, or the oscillation of higher order.

When the relation between the viscosity and the attenuation constant is actually measured at the 0 order oscillation by the above constituted apparatus, the result is shown in FIG. 3(a). On the other hand, when it is measured at the first order oscillation, the result is shown in FIG. 3(b). FIG. 5 shows the graph combined the above two graphs together.

In order to correct the density difference based on the viscosity, if the viscosity-attenuation constant characteristic at the 0 order oscillation is represented by $b0=f(\eta)$, the attenuation constant has a peak at the point of the viscosity $\eta_1$ (which is about 100 mPas in fact). This means that there are two values of the viscosity for the same attenuation constant. Therefore, it causes a trouble, that is which value should be used. If the viscosity-attenuation constant characteristic at the first order oscillation is represented by $b1=g(\eta)$ the viscosity value can be obtained unconditionally from the attenuation constant within comparative wide range. But since the attenuation constant gets peak at the point of the viscosity η(which is about 700 mPas), it is confronted by the same problem as in case of using the 0 order oscillation.

Regarding the test sample, in case it can be predicted whether its viscosity is over or under 700 mPas, it is possible to make use of the viscosity obtained from the first order oscillation. But if the method for correcting the density difference is performed in accordance with the viscosity obtained from the first order oscillation although the viscosity at the 0 order oscillation was measured, there is a defect that it is impossible to expect the high accuracy.

SUMMARY OF THE INVENTION

This invention is proposed in consideration of the above conventional problems. The object of the present invention is to provide the method for deciding the viscosity at the specific order oscillation, even if there is a peak in the viscosity-attenuation constant characteristic at the specific order oscillation, by means of the viscosity-attenuation constant characteristic at the other order oscillation.

In order to achieve the above object, the present invention adopts the following method. Where there is a peak point of the attenuation constant in the viscosity-attenuation constant characteristic of the test sample at the specific order oscillation, the method is to decide whether the attenuation constant of the test sample at the other specific order oscillation is larger or smaller than the value of corresponding to said peak point, to decide according to said decision whether the viscosity detected by the attenuation constant obtained at the specific order oscillation belongs to either side lager or smaller than said peak point, and then to decide the viscosity of the test sample in accordance with the above decisions.

The 0 order which is applied directly to the densimeter is used as the specific order and the the first order is used as the other specific order. According to such arrangement, the viscosity measurement can be performed at the oscillation mode used by the density measurement. Therefore it is possible to expect the improvement of the accuracy of the viscosity measurement.

DESCRIPTION OF THE PREFERRED EMBODIMENTS

Figure 1:
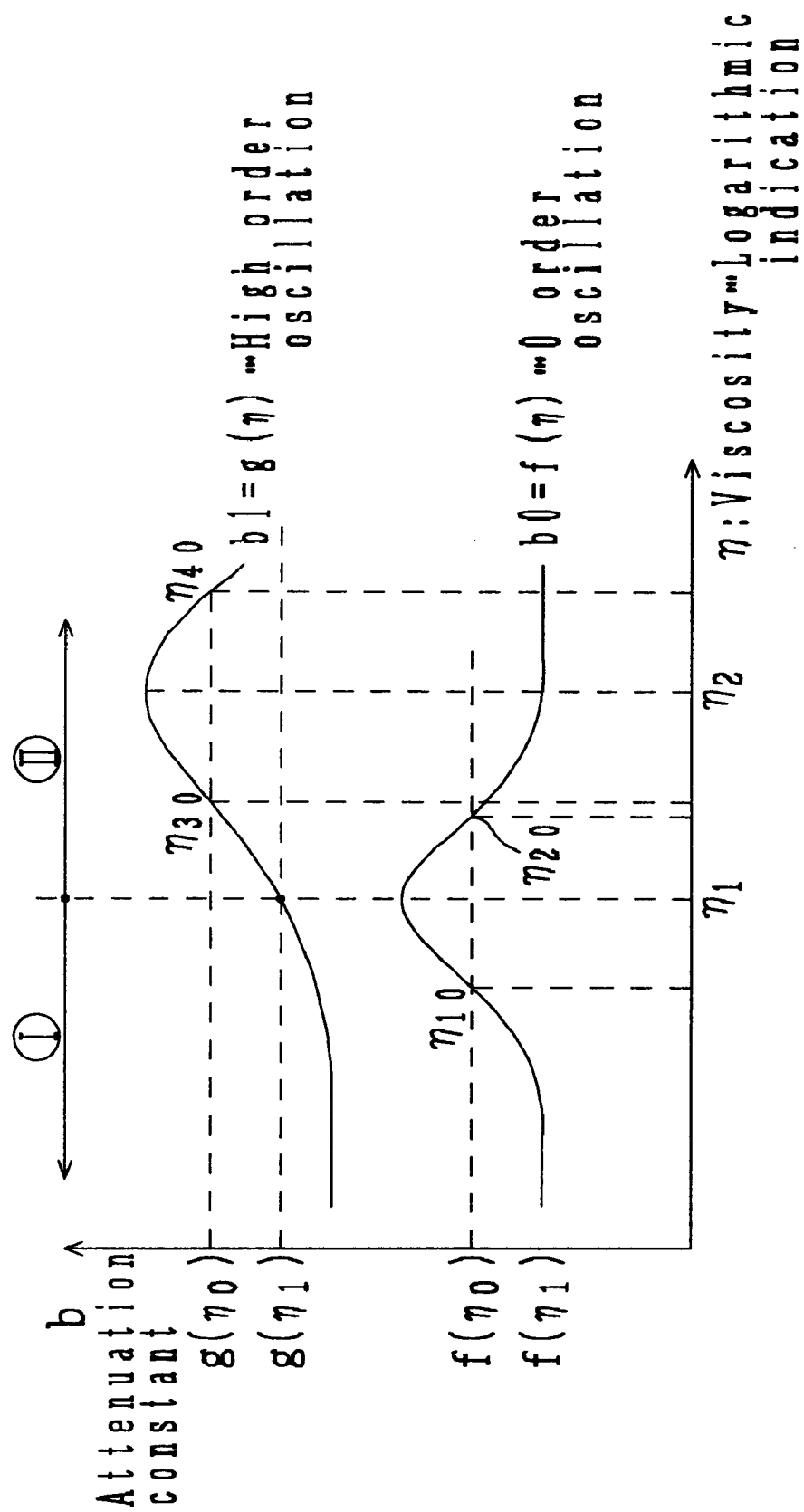
FIG. 1 is a graph showing the viscosity-attenuation constant characteristic at each mode explaining the principle of the present invention.
Figure 2:
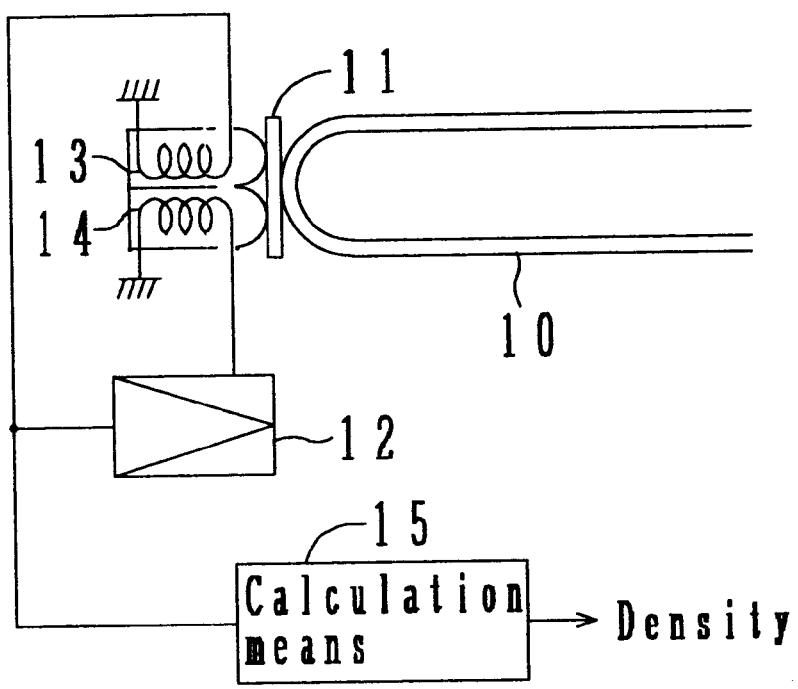
FIG. 2 is the conceptual diagram of the oscillating densimeter.

FIG. 1 is a diagram showing the outline of the present invention.

Figure 5:
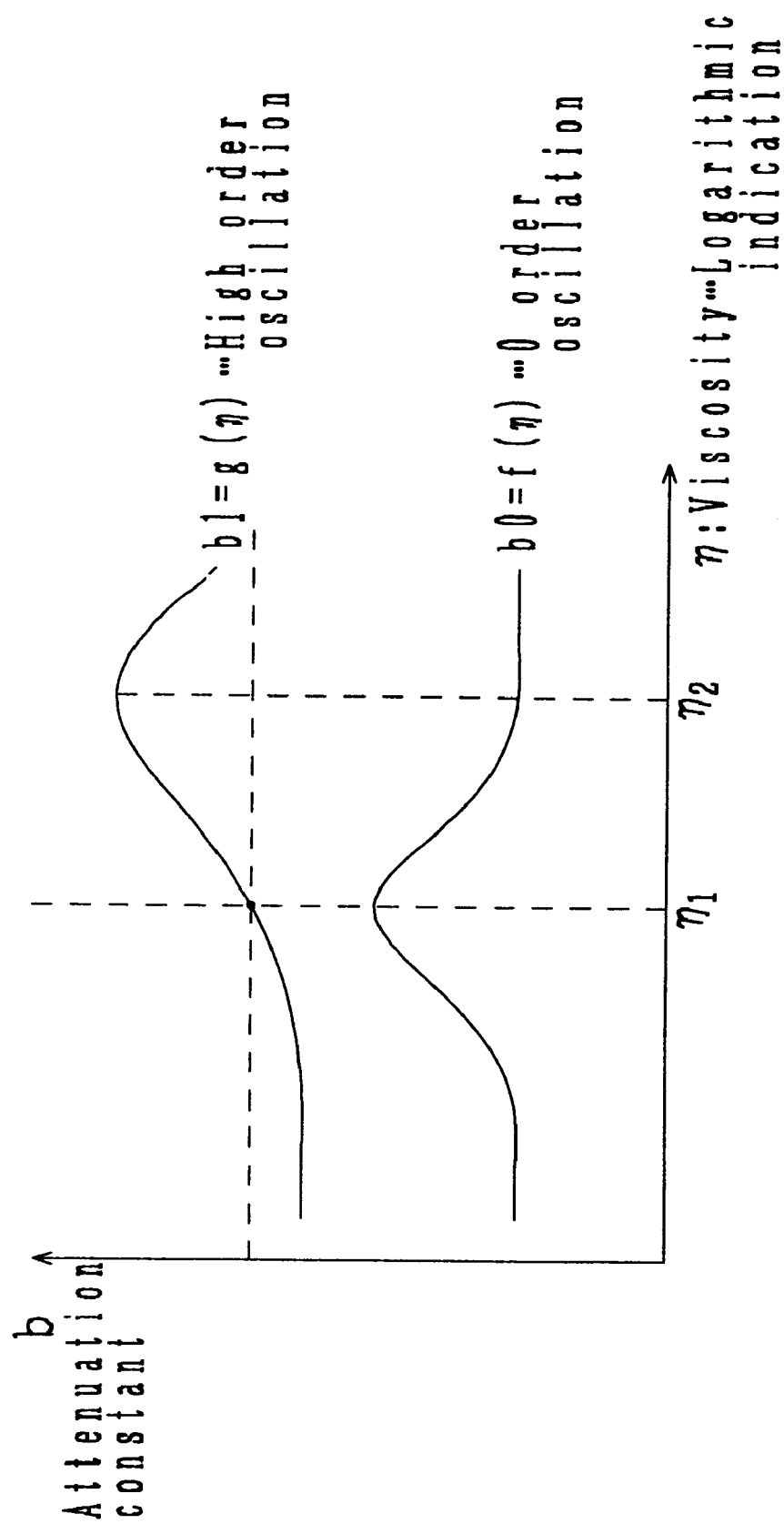
FIG. 5 is a graph showing the viscosity-attenuation constant characteristic at each mode.
Figure 6:
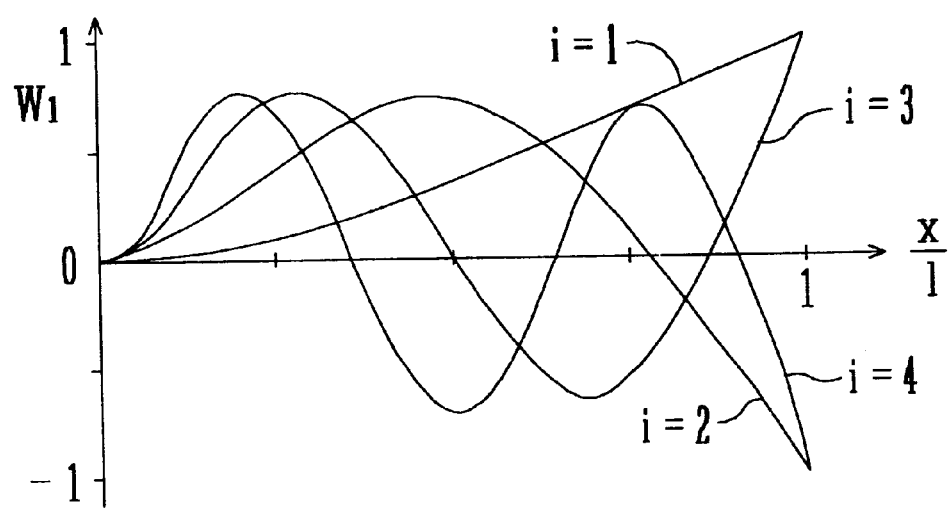
FIG. 6 is a diagram showing a model of the oscillating mode of the U-shaped tube.
Figure 7:
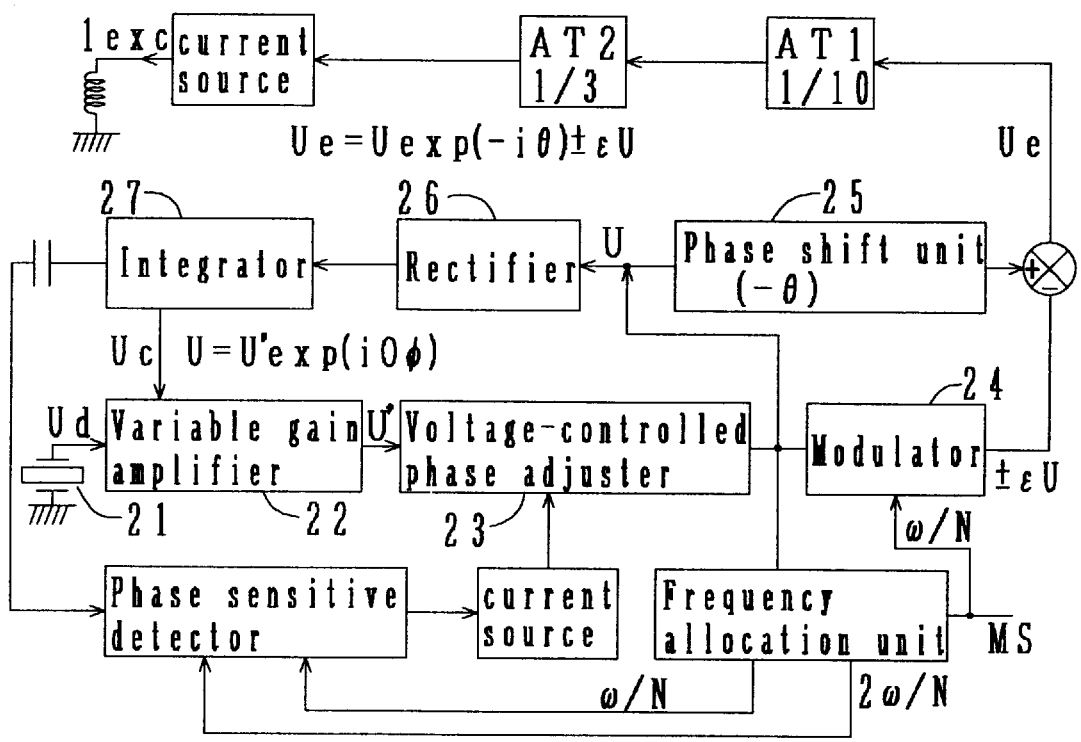
FIG. 7 is a diagram showing a conventional circuit.
Figure 8A:
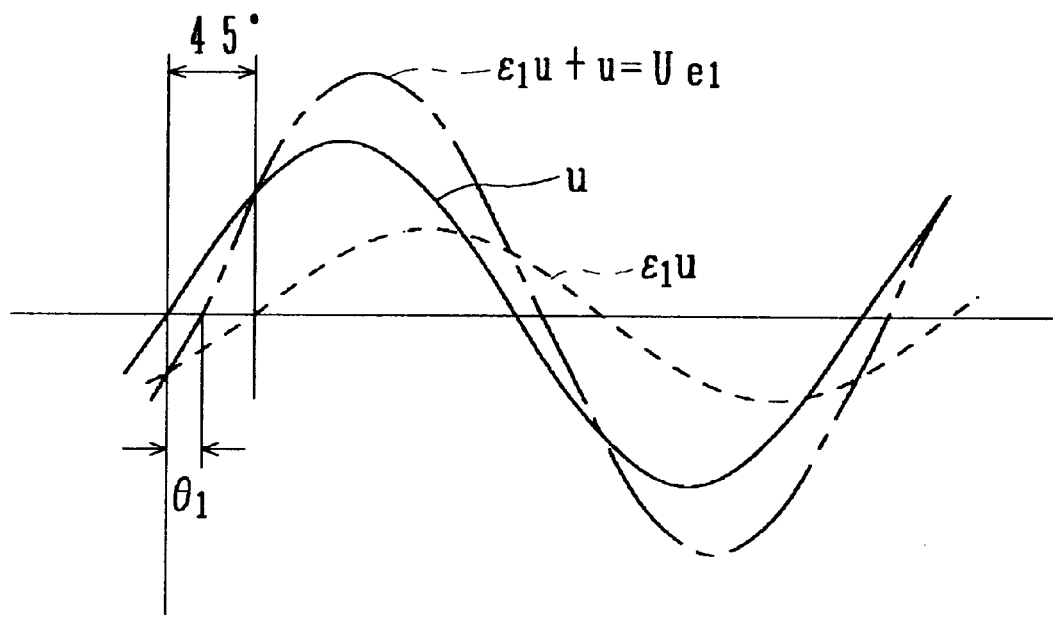
FIG. 8a is a wave-formed diagram showing the phase shift according to the conventional prior art when $0_1$ is greater than $0_2$.
Figure 8B:
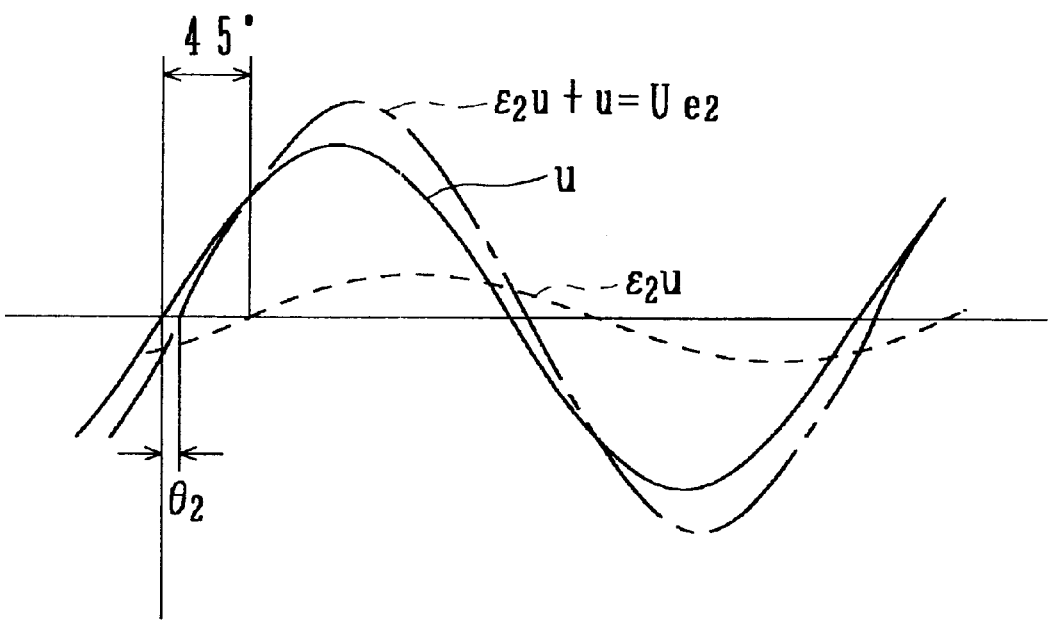
FIG. 8b is a wave formed diagram showing the phase shift according to the conventional prior art when $0_2$ is less than $0_1$.

When the U-shaped tube of the oscillating densimeter is driven by changing the viscosity of the test sample at the 0 order mode, as in FIG. 5, it is possible to obtain the viscosity-attenuation constant curve $b0=f(\eta)$ wherein there is a peak at the viscosity $\eta=\eta_1$. In case of detecting the viscosity of the test sample of the attenuation constant $f(\eta)$ by using that curve, there are two values of the viscosity, that is, $\eta_{10}$ and $\eta_{20}$.

First, by using not only the viscosity-attenuation constant curve at the 0 order oscillation but also one at the first order oscillation mode the viscosity is changed, and then the viscosity-attenuation constant curve $b1=g(\eta)$ has been obtained in advance. On the viscosity-attenuation constant curve $b1=g(\eta)$, the attenuation constant corresponding to the viscosity $\eta=\eta_1$ becomes $g(\eta_1)$. Accordingly, the decision to choose either one from those two viscosity values $\eta_{10}$ and $\eta_{20}$ which can be obtained in accordance with the attenuation constant $f(\eta_0)$ of the viscosity-attenuation constant curve $b0=f(\eta)$ can be made in accordance whether the attenuation constant $g(\eta)$ at the first order oscillation mode is larger than $g(\eta_1)$ or not. In other words, when the attenuation constant $g(\eta)$ is larger than $g(\eta_1)$, the viscosity $\eta_{20}$ at the right of the peak is selected. And when the attenuation constant $g(\eta)$ is smaller than $g(\eta_1)$ the viscosity $\eta_{10}$ at the left of the peak is selected.

The above description refers that the method for deciding the viscosity in accordance with the viscosity-attenuation constant curve at the 0 order $b0=f(\eta)$ makes use of one at the first order $b1=g(\eta)$. According to the same apprehension, the method for deciding the viscosity in accordance with the viscosity-attenuation constant curve at the first order $b1=g(\eta)$ can also make use of one at the 0 order $b0=f(\eta)$.

In other words, the viscosity-attenuation constant curve at the first order $b1=g(\eta)$ becomes peak nearby the viscosity $\eta_2$, and passing by the viscosity $\eta_1$ the curve get to indicate two values of the viscosity for one attenuation constant. Accordingly, how to select one out of two viscosity $\eta_{30}$ and $\eta_{40}$ obtained form the attenuation constant $g(\eta_0)$ is determined by $b0=f(\eta)$ of the viscosity-attenuation constant curve at the 0 order mode. That is to say, the attenuation constant $f(\eta)$ which is obtained from $b0=f(\eta)$ of the viscosity-attenuation constant curve at the 0 order regarding the same test sample is larger than $f(\eta_2)$, and then the viscosity $\eta_{30}$ at the left of the peak is selected. Otherwise, when the attenuation constant $f(\eta)$ is smaller than $f(\eta_2)$, the viscosity $\eta_{40}$ at the right of the peak is selected.

For instance, when the U-shaped tube 10 is vibrating with a frequency of about 200~350 Hz at the 0 order oscillation, the frequency at the first order oscillation (if it is 6.2673 times the frequency at the 0 order oscillation) is about 1253~2194 Hz. And there is a possibility that the characteristic or the viscosity changes within those two frequency band according to the tested object. In general, the above-mentioned density measurement is performed by means of the 0 order oscillation with large amplitude. If the density measurement is performed at the 0 order oscillation, it is preferable to choose the viscosity at the 0 order oscillation because the viscosity is the cause of the density difference and by taking that process it is possible to expect the accurate correction.

Figure 3A:
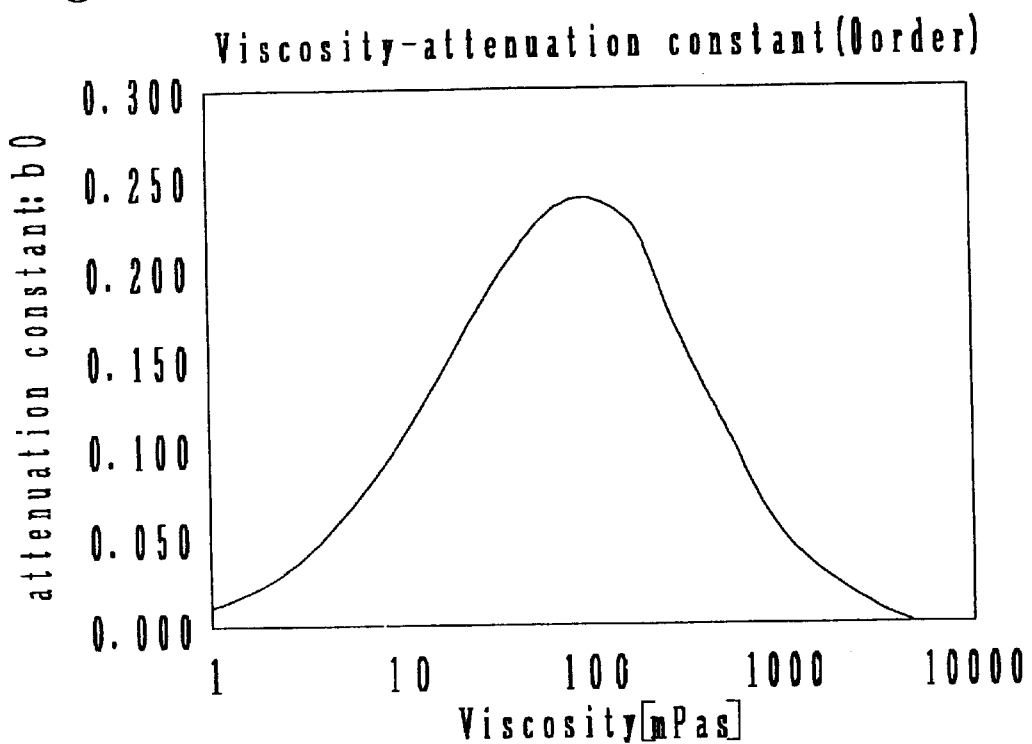
FIG. 3a is a graph showing the density difference in accordance with the viscosity-attenuation constant characteristic at the 0 order mode.
Figure 3B:
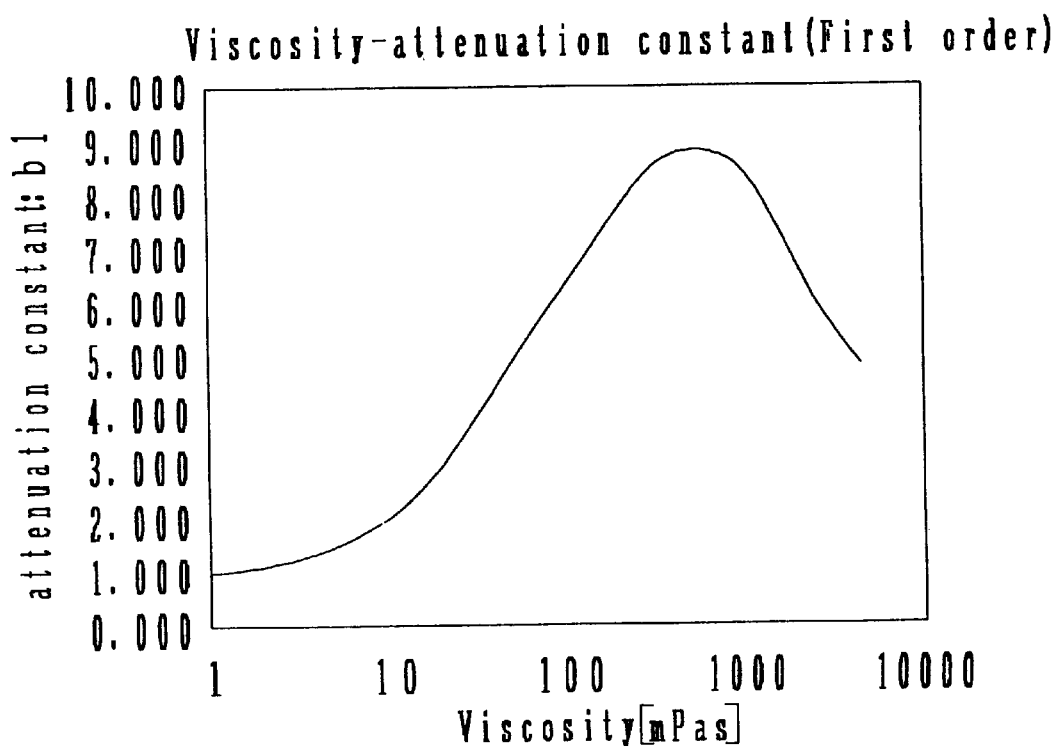
FIG. 3b is a graph showing the density difference in accordance with the viscosity-attenuation constant characteristic at the first order mode.
Figure 4:
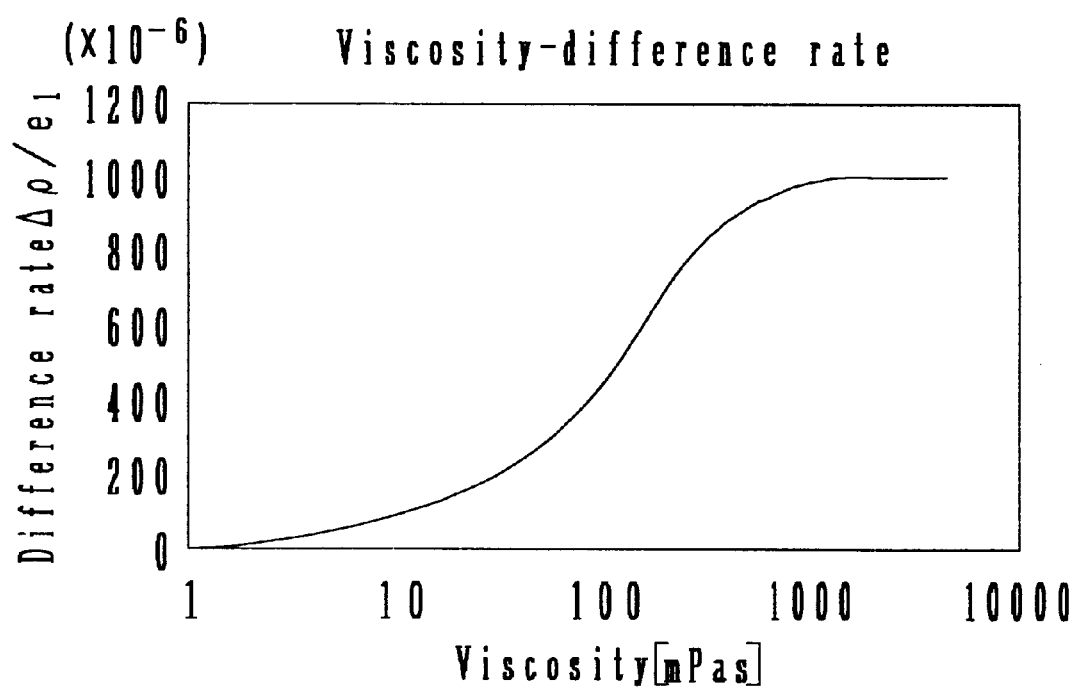
FIG. 4 is a combined graph of two graphs shown in FIGS. 3a and 3b.

Data in Table 1 show tested results made by the method of the present invention described above. Regarding the viscosity reference solution (Sample A)—Newton substance—and sample B~E, the attenuation constants for each are measured at both the 0 order and the first order oscillation. While the viscosities are obtained in accordance with the graphs shown in FIGS. 3(a) and (b) (or in accordance with the specific formula), the densities for each sample are measured at the 0 order oscillation. The densities thus obtained are corrected by each viscosity at both the 0 order and the first order oscillation in accordance with graphs shown in FIG. 4 (or the specific formula), and then the corrected density can be obtained.

As a result of comparing the corrected density thus obtained and the true values of the density (in accordance with the Wardon's pycnometer test), it is found that the corrected densities obtained in accordance with the viscosity at the 0 order oscillation, particularly regarding to the sample B~E, are still more accurate than the other.

The Newton substance described above is a liquid in which the shearing rate is in proportion to the shearing stress, and the viscosity characteristic does not change according to the frequency band. The non-Newton substance is a liquid in which the shearing rate is not in proportion to the shearing stress like the macromolecules substance, and the viscosity characteristic does change according to the frequency band.

two viscosity values for the specific attenuation constant, it is possible to decide the viscosity by making use of the viscosity-attenuation constant characteristics at the other specific order. And since the same order oscillation can be available for both the density measurement and the viscosity measurement, it is possible to improve the measurement accuracy.

What is claimed is:

1. A method for determining values for a fluid viscosity, a fluid density and a density difference resulting from a viscosity correction that corresponds to an amount of compensating the viscosity necessary for correcting the density difference based on the viscosity of a fluid test sample in the density measurement performed by an oscillating densitometer, where the oscillating densitometer has a vibrating member that oscillates a tubular vibrating member filled with a test sample fluid according to an empirical viscosity-attenuation constant characteristic and an attenuation constant during any two specific order oscillations to be selected during a densitometer operation, where there is a peak point on the viscosity-attenuation constant characteristics of the test sample at the one specific order oscillation, which comprises:

deciding whether the attenuation constant measured by means of the viscosity-attenuation constant characteristics of the fluid test sample at another specific order oscillation is larger or smaller than the attenuation constant corresponding to said peak point found for the one specific order oscillation, deciding in accordance with said decision whether the viscosity detected in accordance with the attenuation constant obtained at said one specific order oscillation belongs to either side of larger or smaller than said peak point and

TABLE 1

|  | Order | Attenuation constant | Viscosity Measurement | Density | | | |
|---|---|---|---|---|---|---|---|
|  |  |  |  | Measurement | Corrected density | True value | Difference |
| Sample A (1*) | 0 | 0.242 | 85.8 | 0.856053 | 0.855719 | 0.855721 | −0.000002 |
|  | 1 | 5.391 | 84.1 |  | 0.855723 |  | 0.000002 |
| Sample B (2*) | 0 | 0.239 | 61.6 | 1.918002 | 1.917630 | 1.917622 | 0.000008 |
|  | 1 | 5.926 | 50.5 |  | 1.917674 |  | 0.000052 |
| Sample C (3*) | 0 | 0.113 | 14.589 | 1.877043 | 1.877023 | 1.877031 | −0.000008 |
|  | 1 | 2.663 | 7.068 |  | 1.877061 |  | 0.000003 |
| Sample D (4*) | 0 | 0.290 | 128.1 | 1.934485 | 1.933961 | 1.933955 | 0.000006 |
|  | 1 | 7.506 | 103.2 |  | 1.934056 |  | 0.000101 |
| Sample E (5*) | 0 | 0.011 | 1880.4 | 1.968810 | 1.967058 | 1.967008 | 0.000005 |
|  | 1 | 11.013 | 431.6 |  | 1.967487 |  | 0.000479 |

(Note)
(1*) Viscosity reference substance
(2*) Lubricating oil made by Daikin Kogyo Kabushiki Kaisha (Product Name: Dyfuroile, Product No. 3)
(3*) Lubricating oil made by Daikin Kogyo Kabushiki Kaisha (Product Name: Dyfuroile, Product No. 2)
(4*) Lubricating oil made by Daikin Kogyo Kabushiki Kaisha (Product Name: Dyfuroile, Product No. 10)
(5*) Lubricating oil made by Daikin Kogyo Kabushiki Kaisha (Product Name: Dyfuroile, Product No. 20)

The foregoing relates to a preferred exemplary embodiment of the invention, it being understood that other variants and embodiments thereof are possible within the spirit and scope of the invention, the latter being defined by the appended claims.

According to the present invention as described above, even if the viscosity-attenuation constant characteristic at the specific order has a peak, that is to say even if there is deciding the viscosity of the test sample according to the results of the above two decisions.

2. A method for deciding the viscosity as defined in claim 1, wherein the 0 order is used as the one specific order and a first order is used as the another specific order of oscillation during said densitometer operation.

\* \* \* \* \*